United States Patent [19]
Narai et al.

[11] Patent Number: 5,256,213
[45] Date of Patent: Oct. 26, 1993

[54] BEARING STEEL

[75] Inventors: Hiroshi Narai, Fujisawa; Tsutomu Abe, Chigasaki; Kazuhiro Uemura, Kanagawa, all of Japan

[73] Assignee: NSK Ltd., Tokyo, Japan

[21] Appl. No.: 913,699

[22] Filed: Jul. 16, 1992

[30] Foreign Application Priority Data

Jul. 18, 1991 [JP] Japan .................... 3-178192

[51] Int. Cl.$^5$ .............................................. C22C 38/00
[52] U.S. Cl. ...................................... 148/320; 148/906
[58] Field of Search ............... 384/492, 548, 912, 625; 148/906, 320

[56] References Cited

U.S. PATENT DOCUMENTS

| | | | |
|---|---|---|---|
| 4,927,601 | 5/1990 | Iikubo et al. | 148/906 |
| 4,992,111 | 2/1991 | Yamada et al. | 148/906 |
| 5,011,304 | 4/1991 | Murakami et al. | |

FOREIGN PATENT DOCUMENTS

2155951 10/1985 United Kingdom .
2236762 4/1991 United Kingdom .

*Primary Examiner*—Deborah Yee
*Attorney, Agent, or Firm*—Sughrue, Mion, Zinn, Macpeak & Seas

[57] ABSTRACT

In order to produce bearing steels of long life and high reliability with a higher probability by utilizing parameters for cleanness evaluation that are related to the shortest life of bearings, in the present invention, the logarithmic decrease in the cumulative size distribution of oxide-type nonmetallic inclusions and the estimated maximum diameter of inclusion particles present per unit volume or unit area are determined from the particle size distribution of the oxide-type nonmetallic inclusions, and the cleanness of interest is specified on the basis of said logarithmic decrease or said estimated maximum inclusion diameter.

10 Claims, 3 Drawing Sheets

5,256,213

BEARING STEEL

BACKGROUND OF THE INVENTION

Field of Industrial Utility

The present invention relates to a bearing steel, more particularly to a bearing steel that is capable of providing long-lived bearings suitable for use in automobiles, agricultural machines, construction machines and iron- and steel-making machines, especially for use in their transmissions and engines.

Prior Art

Nonmetallic inclusions, in particular oxide-type inclusions, that are present in steels are known to increase the frequency of breakage when the steels are worked, for example, drawn to wires, whereby the mechanical properties of the steel product such as the number of twists and fatigue are deteriorated. In addition, if rolling members such as bearings that are made of steels containing oxide-type nonmetallic inclusions are subjected to cyclic stresses of rolling contact, the inclusions become the start point for the propagation of microcracking, which continues to develop until flaking occurs, whereupon the life of the bearing comes to an end.

Under these circumstances, various kinds of ultra-clean steels of low oxygen content have been proposed; for example, Unexamined Published Japanese Patent Application No. 76916/1978 discloses an ultra-clean steel with the oxygen content being adjusted to no more than 50 ppm.

The quality of steel members is largely dependent on the number and size of oxide-type nonmetallic inclusions. The number and size of such inclusions are conventionally checked by the methods described in JIS G 0555 and ASTM E 45 (see Unexamined Published Japanese Patent Application No. 309844/1988). Also disclosed in the prior art is an apparatus for inspecting the image of inclusions by an image processing method.

The life of bearings is closely related to the cleanness of bearing steels and it is common practice to extend the life of bearings by designating the oxygen level of steels or an inclusion index based on ASTM standards A conventional method of evaluating oxide-type inclusions is described by Saitoh et al in "Development of A Method for Evaluating Inclusions by Electron Beam Technique", Japan Society for the Promotion of Science, 5-1 to 5-14, May 19, 1987; according to this method, inclusions in a sample steel are made afloat on the surface by the electron beam technique and the amount, morphology and composition of the inclusions are quantitated.

However, this conventional method does not provide specific information about the range of the number and size of oxide-type inclusions that is effective for the purpose of improving the fatigue life of bearings and, hence, no relationship that will assure a satisfactory life has been known with respect to the conventional bearings. Further, as the demand for achieving even higher levels of cleanness has arisen in recent years, it has become difficult to predict a long-lived bearing from a short-lived one solely by means of the heretofore used parameters for evaluating cleanness and it is no longer possible to achieve a further improvement in the life of bearings merely by designating those parameters.

With a view to overcoming this difficulty, it has been proposed in Unexamined Published Japanese Patent Application No. 126839/1991 that the average particle size of inclusions, the number of their particles present and their relative abundance be limited to lie within specified ranges whereas the oxygen concentration should be held below a specified value, so that long-lived bearing steels and ball-and-roller bearings can be provided.

However, even the method disclosed in that patent application has had the problem that it occasionally yields short-lived bearings, although the incidence is not higher than 0.1%.

SUMMARY OF THE INVENTION

The present invention has been accomplished under these circumstances and has as an object providing bearing steels of long life and high reliability with a higher manufacturing probability by utilizing parameters for cleanness evaluation that are related to the shortest life of bearings.

This object to the present invention can be attained by a bearing steel with which the logarithmic decrease in the cumulative size distribution of oxide-type nonmetallic inclusions and the estimated maximum diameter of inclusion particles present per unit volume or unit area are determined from the particle size distribution of the oxide-type nonmetallic inclusions, with the cleanness of that bearing steel being established on the basis of said logarithmic decrease or said estimated maximum diameter of inclusion particles.

DETAILED DESCRIPTION OF THE PREFERRED EMBODIMENTS

Figure 1:
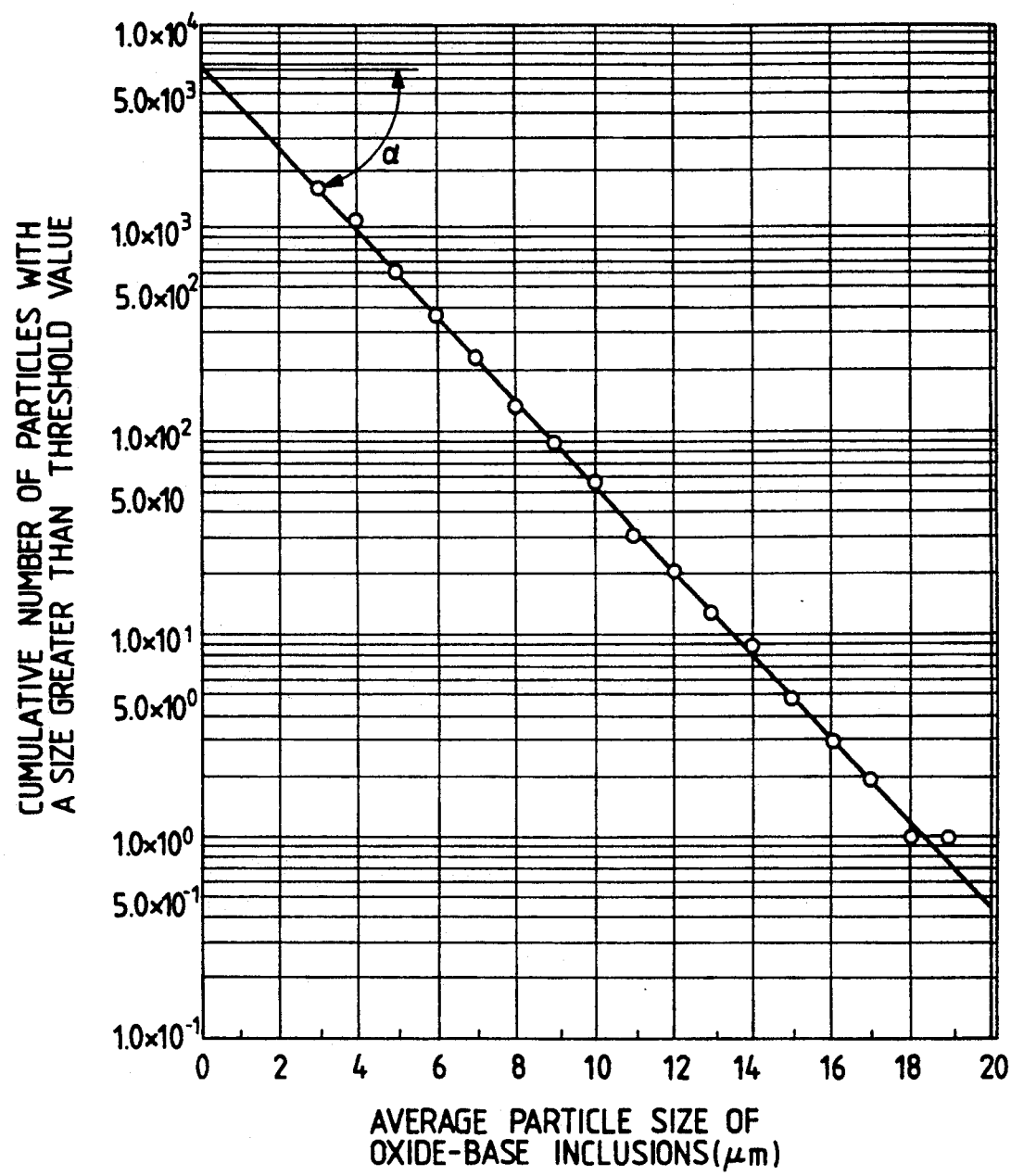
FIG. 1 is a graph showing the correlation between the average particle size of oxide-type inclusions in the bearing steel of the present invention and the cumulative number of inclusion particles with a size greater than a threshold value (in exponential terms)

As a result of their intensive studies conducted in order to attain the aforementioned object of the present invention, the inventors found that the distribution of the particles of oxide-type inclusions could be approximated by an exponential function. As it turned out, the particle size distribution of oxide-type inclusions enabled their cumulative distribution to be approximated by a straight line as shown in FIG. 1, which plots the average particle size of oxide-type inclusions on the x-axis whereas the cumulative number of particles with a size greater than a threshold value is potted exponentially on the y-axis.

Figure 2:
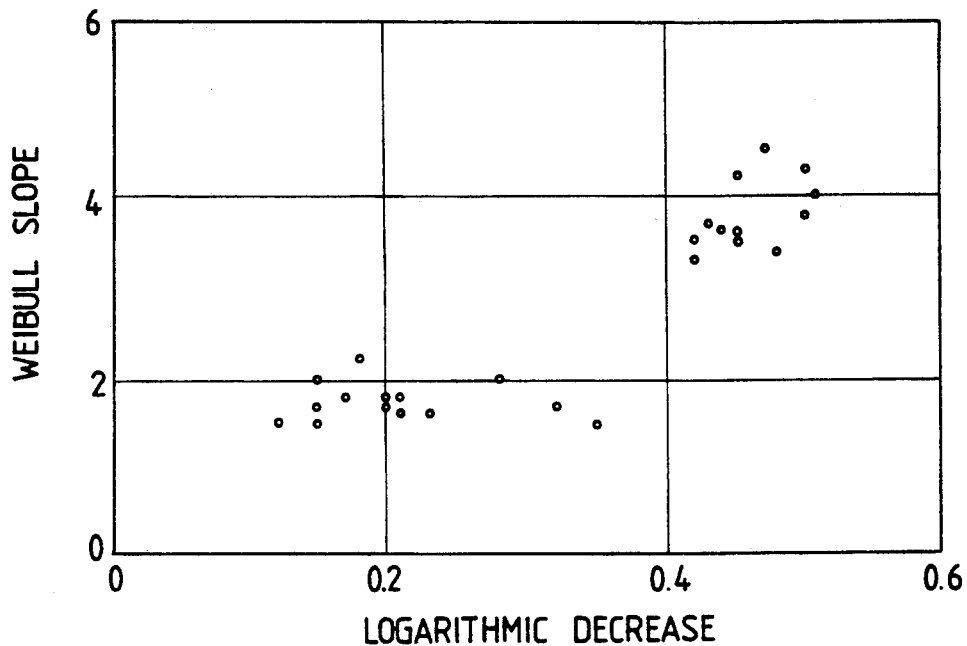
FIG. 2 is a graph showing the correlation between the logarithmic decrease in the cumulative size distribution of oxide-type inclusions in the bearing steel of the present invention and the Weibull slope.

Further, the present inventors conducted a thrust life ($L_{10}$) test on bearing samples that had the same ratio of observed life to calculated life ($L_{10}/L_{10cal}$) but which differed in the shortest life; as a result, it was found that the Weibull slope saw a sharp increase with samples that exceeded a certain value of the slope of the straight line of approximation (tan α), namely, the logarithmic decrease in the cumulative size distribution of oxide-type inclusions. As the Weibull slope increases, the life of a long-lived bearing becomes close to that of a short-lived bearing and the variation in the life of bearings becomes so small as to enable the production of long-lived bearings with a higher probability. FIG. 2 is a graph showing the result of investigating the correlation between logarithmic decrease and Weibull slope as regards several different charges of SCR 440 that exhibited substantially the same level of $L_{10}$. As it turned out, when the logarithmic decrease per 1 μm was 0 4 and more, the Weibull slope increased sharply and the variation in the life of bearings became so small as to enable the production of long-lived bearings with a higher probability. On the basis of these data, one can confidently conclude that the logarithmic decrease in the cumulative size distribution of oxide-type inclusions is advantageously adjusted to 0.4 or more in order to attain the object of the present invention.

In the case where the logarithmic decrease in the cumulative size distribution of oxide-type inclusions is more than 0.6, there is a problem in cost. Practically, the logarithmic decrease is preferably in the range of 0.4–0.6.

The foregoing discussion is directed to the case where the average particle size distribution of oxide-type inclusions can be approximated by an exponential function; however, this is not the sole case of the present invention and it may be applied to other cases, i.e., where the relationship between the average particle size distribution and the cumulative number of particles with a size greater than a threshold value can substantially be approximated by a straight line or where the distribution of estimated maximum inclusions is statistically related by a substantial straight line with respect to their cumulative distribution function, and in those cases, the present invention can be applied on the basis of the gradient of the straight line of approximation or correlation.

Figure 3:
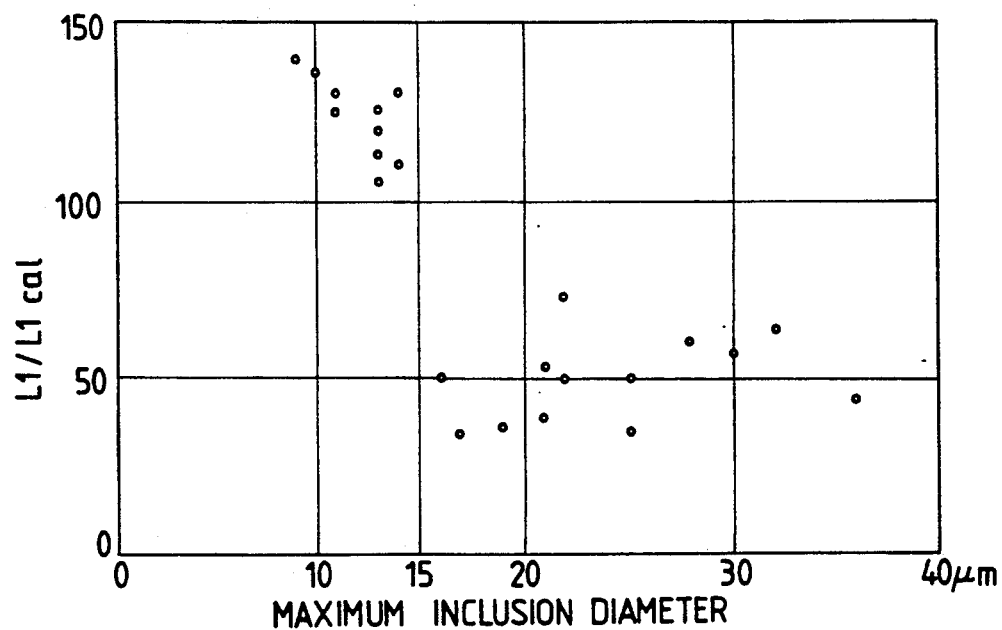
FIG. 3 is a graph showing the correlation between the maximum diameter of oxide-type inclusions in the bearing steel of the present invention and $L_1/L_{1cal}$.
Figure 4:
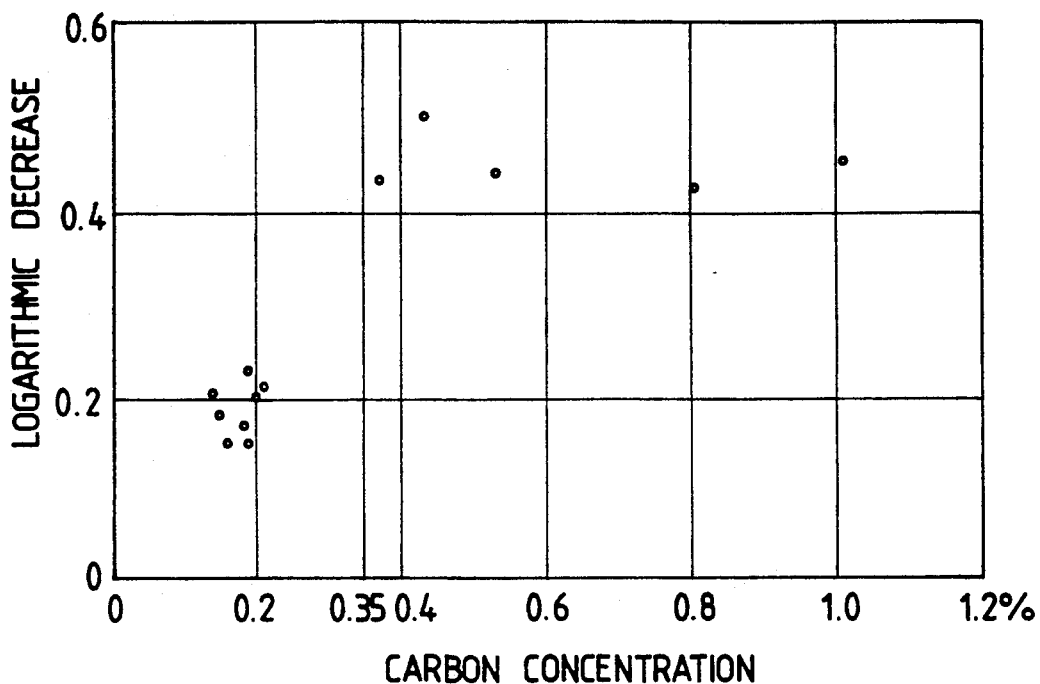
FIG. 4 is a graph showing the correlation between the concentration of carbon in the bearing steel of the present invention and the logarithmic decrease in the cumulative size distribution of oxide-type inclusions.
Figure 5:
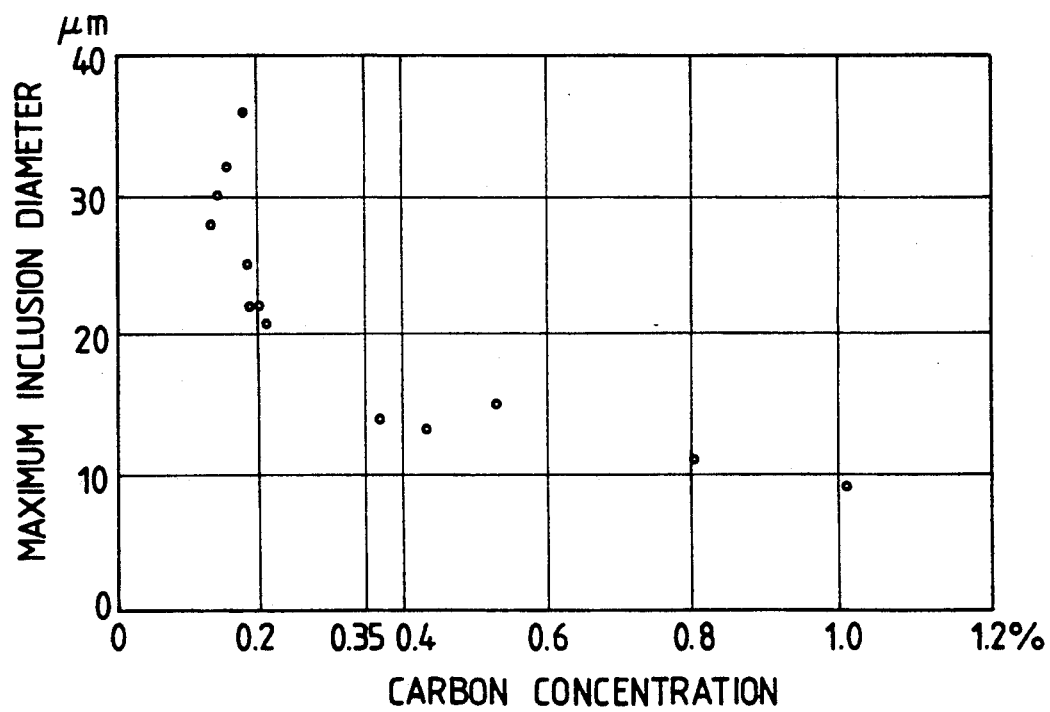
FIG. 5 is a graph showing the correlation between the concentration of carbon in the bearing steel of the present invention and the maximum diameter of oxide-type inclusions.

The present inventors also conducted a thrust life ($L_1$) test to investigate how the estimated values of maximum inclusion diameter per cubic centimeter as obtained by statistical analyses of extreme correlated to the ratio of observed bearing life to calculated life ($L_1/L_{1cal}$); as a result, it was found that $L_1/L_{1cal}$ changed sharply when the maximum inclusion diameter exceeded a certain level. The index $L_1/L_{1cal}$ is such that one may safely conclude that a bearing of interest has the longer life as the value of $L_1/L_{1cal}$ increases. FIG. 3 is a graph showing the result of investigating the correlation between the maximum inclusion diameter per cubic centimeter and $L_1/L_{1cal}$ as regards several different charges of a particular bearing steel (SUJ 2). As it turned out, when the maximum inclusion diameter was 15 μm and less, $L_1/L_{1cal}$ increased sharply to improve the life of bearings. On the basis of those data, one can confidently conclude that the estimated value of the maximum inclusion diameter per cubic centimeter is advantageously adjusted to 15 μm or less in order to attain the object of the present invention.

In the case where the estimated value of the maximum inclusion diameter per cubic centimeter is less than 3 μm, there is a problem in cost. Practically, the estimated value of the maximum inclusion diameter per cubic centimeter is preferably in the range of 3 μm–15 μm.

The foregoing discussion is directed to the maximum inclusion diameter per unit volume (1 cm$^3$) but this is by no means the sole case of the present invention and same results can be obtained even if an investigation is conducted on the maximum inclusion diameter per unit area.

The aforementioned thrust life tests were conducted on disk-shaped specimens of bearing using a testing machine of the type described in "Tokushuko Binran (Handbook of Specialty Steels)", First Edition, compiled by Denki Seikosho, published by Rikogakusha, May 25, 1965, pp. 10 to 21. The testing conditions were as follows:

Pmax = 500 kgf/mm$^2$
N = 3000 cpm
Lubricant = Turbine oil VG 68

Trust life $L_{10}$ is equivalent to the cumulative number of revolutions up to the point of time when 10% of the test specimens of each sample came to the end of their life; thrust life $L_1$ is equivalent to the cumulative number of revolutions up to the point of time when 1% of the test specimens of each sample came to the end of their life.

Statistical analyses of extreme were conducted in accordance with the technique described in "Kiron (Transaction of the Japan Society of Mechanical Engineers)", 55–509, p.58, 1989; the test area was 80 mm$^2$; and the total test area was 3200 mm$^2$.

Alternatively, the logarithmic decrease in the cumulative size distribution of oxide-type inclusions is defined by $\log\{F(X+1)/F(X)\}$, where $F(X)$ is the total number of inclusions larger than a specified size (average diameter = X μm). This parameter corresponds to tan α, or the gradient of the aforementioned straight line of approximation or correlation.

The confidence coefficient for computing $L_1/L_{1cal}$ was set at 0.21.

To guarantee the shortest life of bearings mentioned above, mere improvement of the life by increasing $L_1/L_{1cal}$ is insufficient and it is also necessary to insure that the Weibull slope is large enough to achieve satisfactory suppression of the variation in life. Stated more specifically, bearings of long life and high reliability can only be provided with a higher probability if the value of $L_1/L_{1cal}$ is increased to improve the life of bearings per se if the Weibull slope is increased to insure that long-lived bearings will exist with a higher probability. Hence, the aforementioned two conditions must be satisfied simultaneously.

The maximum inclusion diameter can be guaranteed by a high-precision method for 3D evaluation that involves measurement on oxide-type inclusions extracted from a steel sample, for example, by a method that involves melting and extraction with an electron beam.

If the steel of the present invention is to be produced by ordinary processes for mass production which comprise melting in a large-size electric furnace, eccentric bottom tapping, ladle refining (by ladle furnace), RH degassing and vertical type bloom continuous casting, the two conditions relating to logarithmic decrease and maximum oxide inclusion diameter set forth above can be met by optimizing at high levels the temperature for blowing from the bottom of the electric furnace and the tapping temperature, adjusting the slab composition and the timing of deoxidation, and adjusting the intensity of agitation in the LF refining and RH degassing. Hence, the range over which those two conditions can be met effectively may be subject to a certain constraint by the composition of the alloy. Under the circumstances, the present inventors investigated both the correlation between the logarithmic decrease in the cumulative size distribution of oxide-type inclusions and the carbon concentration before heat treatment and the correlation between the estimated maximum inclusion diameter and the carbon concentration before heat treatment. The results are shown in Tables 4 and 5, from which one can see that the logarithmic decrease increases and the maximum inclusion diameter decreases if the carbon concentration is 0.35% and above. Hence, one can confidently conclude that the carbon concentration before heat treatment is advantageously adjusted to 0.35% and more.

In the case where the carbon concentration is less than 0.35%, it is difficult to conduct the cumulative size distribution of the oxide-type nonmetallic inclusions on a statistical analyses of the extreme. Practically, the carbon concentration is preferably not less than 0.35 %.

EXAMPLES

Examples of the present invention are described below.

EXAMPLE 1

The different charges of bearing steel (SUJ 2) were worked, quenched and tempered to prepare disk-shaped test samples. For each of these disk-shaped samples, the following parameters were investigated: the logarithmic decrease per $\mu$m; the maximum diameter of oxide-type inclusions as estimated per cubic centimeter; the maximum diameter of oxide-type inclusions as measured by a method of evaluation involving melting and extraction with an electron beam; Weibull slope; and service life ($L_1/L_{1cal}$). The results are shown in Table 1. The particle size distribution profile of oxide-type inclusions was quantitated with an optical microscopic image analyzer on part of the samples under the life test by the method described in "Zairyo to Purosesu (Materials and Process)", vol. 4, p. 321, 1991. When measuring the maximum diameter of oxide-type inclusions by a method of evaluation involving melting and extraction with an electron beam, an apparatus of the type described in "Tetsu to Hagane (Iron and Steel)", vol. 75, No. 10, pp. 83 to 99, 1989 was used to melt the sample at an acceleration voltage of 10 kV and at a beam current of 60 mA for a beam scan coverage of 40% and for an exposure time of 8 sec. After cooling, the sample was subjected to measurement with a SEM (scanning electron microscope) image analyzer. The life test was conducted by the same method as described under "Mechanism of Action".

TABLE 1

| Charge No. | Log-arithmic decrease | Maximum inclusion diameter ($\mu$m) | | Carbon concentration (%) | Weibull slope | Service life $L_1/L_{1cal}$ |
|---|---|---|---|---|---|---|
| | | Estimated | Found | | | |
| 1 | 0.51 | 10 | 11 | 1.0 | 4.0 | 136 |
| 2 | 0.45 | 13 | 12 | 1.0 | 3.5 | 125 |
| 3 | 0.48 | 14 | 15 | 1.0 | 3.4 | 110 |
| 4 | 0.47 | 9 | 10 | 1.0 | 4.5 | 140 |
| 5 | 0.42 | 11 | 12 | 1.0 | 3.5 | 125 |
| 6 | 0.35 | 14 | 13 | 1.0 | 1.5 | 130 |
| 7 | 0.21 | 13 | 14 | 1.0 | 1.8 | 115 |
| 8 | 0.45 | 19 | 20 | 1.0 | 3.6 | 37 |

TABLE 1-continued

| Charge No. | Log-arithmic decrease | Maximum inclusion diameter ($\mu$m) | | Carbon concentration (%) | Weibull slope | Service life $L_1/L_{1cal}$ |
|---|---|---|---|---|---|---|
| | | Estimated | Found | | | |
| 9 | 0.50 | 21 | 25 | 1.0 | 3.8 | 39 |
| 10 | 0.32 | 25 | 27 | 1.0 | 1.7 | 35 |

As one can see from Table 1, the samples (charge Nos. 1 to 5) that satisfied the requirement that the logarithmic decrease per $\mu$m be at least 0.4 and that neither of the estimated and found values of the maximum diameter of oxide-type inclusions per cubic centimeter be more than 15 $\mu$m showed by far greater values of Weibull slope and $L_1/L_{1cal}$ than the other sample (change Nos. 6 to 10). These data show that the bearing steels of charge Nos. 1 to 5 can provide long-lived bearings with a higher probability.

In Example 1, the maximum diameter of oxide-type inclusions was measured by a method of evaluation involving melting and extraction with an electron beam and this offered the advantage of insuring a higher precision of evaluation.

EXAMPLE 2

Steels having ten different carbon concentrations as listed in Table 2 were treated and worked into disk-shaped samples as in Example 1; thereafter, the following parameters were investigated for each sample as in Example 1: the logarithmic decrease per $\mu$m; the maximum diameter of oxide-type inclusions as estimated per cubic centimeter; o the maximum diameter of oxide-type inclusions as measured by a method of evaluation involving melting and extraction with an electron beam; Weibull slope; and service life ($L_1/L_{1cal}$). The results are also shown in Table 2.

TABLE 2

| Charge No. | Carbon concentration (%) | Log-arithmic decrease | Maximum inclusion diameter ($\mu$m) | | Weibull slope | Service life $L_1/L_{1cal}$ |
|---|---|---|---|---|---|---|
| | | | Estimated | Found | | |
| 1 | 1.01 | 0.45 | 9 | 8 | 4.2 | 140 |
| 2 | 0.81 | 0.42 | 11 | 12 | 3.3 | 106 |
| 3 | 0.53 | 0.44 | 15 | 14 | 3.6 | 111 |
| 4 | 0.43 | 0.50 | 13 | 15 | 4.3 | 123 |
| 5 | 0.37 | 0.43 | 14 | 13 | 3.7 | 136 |
| 6 | 0.20 | 0.20 | 22 | 21 | 1.7 | 50 |
| 7 | 0.21 | 0.21 | 21 | 23 | 1.6 | 52 |
| 8 | 0.19 | 0.23 | 22 | 25 | 1.6 | 72 |
| 9 | 0.14 | 0.20 | 28 | 30 | 1.8 | 60 |
| 10 | 0.16 | 0.15 | 32 | 29 | 1.5 | 64 |

As one can see from Table 2, the samples (charge Nos. 1 to 5) with carbon concentrations (%) of at least 0.35% were such that the logarithmic decrease increased markedly whereas the maximum diameters of oxide-type inclusions (both estimated and found) decreased markedly compared to the other samples (charge Nos. 6 to 10). It was also confirmed that charge Nos. 1 to 5 satisfied the requirement that the logarithmic decrease per 1.0 $\mu$m be at least 0.4 and that neither of the estimated and found values of the maximum diameter of oxide-type inclusions per cubic centimeter be more than 15 $\mu$m, thereby enabling the production of long-lived bearings with a higher probability.

In Example 2, the maximum diameter of oxide-type inclusions was measured by a method of evaluation involving melting and extraction with an electron beam and this offered the advantage of insuring a higher precision of evaluation.

In Examples 1 and 2, SUJ 2 was used as a bearing steel but this is by no means the sole case of the present invention and other species of bearing steel such as SUJ 3 and SUJ 4 may of course be employed.

In Examples 1 and 2, the maximum inclusion diameter of oxide-type inclusions was investigated for unit volume (1 cm$^3$) but this is by no means the sole case of the present invention and the maximum inclusion diameter of oxide-type inclusions may be investigated for unit area.

ADVANTAGES OF INVENTION

As described on the foregoing pages, the cleanness of the bearing steel of the present invention is estimated by such a method that the logarithmic decrease in the cumulative size distribution of oxide-type nonmetallic inclusions and the estimated maximum diameter of inclusion particles present per unit volume or unit area are determined from the particle size distribution of the oxide-type nonmetallic inclusions, and the cleanness of interest is specified on the basis of said logarithmic decrease or said estimated maximum diameter of inclusion particles. In this way, the Weibull slope is increased by a sufficient degree to reduce the variation in the service life of bearings. Further, the value of $L_1/L_{1cal}$ can be increased markedly to achieve improvement in the life of bearings.

As a result, the present invention offers the advantage that long-lived bearings of improved reliability can be produced with a higher probability.

What is claimed is:

1. A bearing steel comprising oxide-type nonmetallic inclusions, wherein the cumulative size distribution of said oxide-type nonmetallic inclusions comprises a logarithmic decrease in average particle size diameter per 1 $\mu$m of 0.4 to 0.6.

2. The bearing steel of claim 1, wherein said oxide-type nonmetallic inclusions have a maximum particle diameter of 3 $\mu$m to 15 $\mu$m per cubic centimeter.

3. The bearing steel of claim 1, further comprising a carbon concentration before heat treatment of at least 0.35%.

4. The bearing steel of claim 1, further comprising a carbon concentration before heat treatment in the range of 0.35% to 1.01%.

5. The bearing steel of claim 1, wherein said oxide-type nonmetallic inclusions have a maximum particle diameter of 3 $\mu$m to 15 $\mu$m per cubic centimeter, and further comprising a carbon concentration before heat treatment of at least 0.35%.

6. A steel bearing comprising oxide-type nonmetallic inclusions, wherein the cumulative size distribution of said oxide-type nonmetallic inclusions comprises a logarithmic decrease in average particle size diameter per 1 $\mu$m of 0.4 to 0.6.

7. The steel bearing of claim 6, wherein said oxide-type nonmetallic inclusions have a maximum particle diameter of 3 $\mu$m to 15 $\mu$m per cubic centimeter.

8. The steel bearing of claim 6, further comprising a carbon concentration before heat treatment of at least 0.35%.

9. The steel bearing of claim 6, further comprising a carbon concentration before heat treatment in the range of 0.35% to 1.01%.

10. The steel bearing of claim 6, wherein said oxide-type nonmetallic inclusions have a maximum particle diameter of 3 $\mu$m to 15 $\mu$m per cubic centimeter, and further comprising a carbon concentration before heat treatment of at least 0.35%.

* * * * *